(12) United States Patent
Chandrasekar et al.

(10) Patent No.: US 9,108,324 B1
(45) Date of Patent: Aug. 18, 2015

(54) PIN CUTTER

(75) Inventors: N. R. Chandrasekar, Canton, MA (US);
Donald McKay, Belmont, MA (US);
Andrew E. Goddard, Beverly, MA (US)

(73) Assignee: IQ Medical Devices, LLC, Belmont, MA (US)

(*) Notice: Subject to any disclaimer, the term of this patent is extended or adjusted under 35 U.S.C. 154(b) by 830 days.

(21) Appl. No.: 13/253,129

(22) Filed: Oct. 5, 2011

Related U.S. Application Data

(60) Provisional application No. 61/389,824, filed on Oct. 5, 2010.

(51) Int. Cl.
*B26B 17/00* (2006.01)
*B26D 1/00* (2006.01)

(52) U.S. Cl.
CPC ............ *B26B 17/00* (2013.01); *B26B 17/006* (2013.01); *B26D 1/00* (2013.01)

(58) Field of Classification Search
CPC .... B26B 17/00; B26B 17/003; B26B 17/006; B26B 17/02

USPC ............ 30/124, 28, 109, 111–113, 92, 501, 30/502, 173, 175, 178, 186, 190, 192, 187, 30/231, 232, 244, 251
See application file for complete search history.

(56) References Cited

U.S. PATENT DOCUMENTS

| | | | | |
|---|---|---|---|---|
| 2,615,181 | A * | 10/1952 | McGaughey | 7/133 |
| 3,310,872 | A * | 3/1967 | Dowdell | 30/187 |
| 4,815,476 | A * | 3/1989 | Clossick | 600/564 |
| 5,327,896 | A * | 7/1994 | Schmieding | 600/566 |
| 7,992,305 | B1 * | 8/2011 | Herrick | 30/95 |
| 2001/0022029 | A1 * | 9/2001 | Vary | 30/228 |
| 2011/0203116 | A1 * | 8/2011 | Vary | 30/187 |

* cited by examiner

*Primary Examiner* — Phong Nguyen
(74) *Attorney, Agent, or Firm* — David M. Driscoll, Esq.

(57) ABSTRACT

A pin cutter that includes a housing having at a proximal end thereof a grip, an actuator handle supported at the housing, a pair of elongated blades that define at a distal end thereof a set of cutting jaws, a ramp mechanism secured with the actuator handle for operating proximal ends of the blade member, a hollow shaft extending through the housing, the ramp mechanism supported about the hollow shaft, and a biasing spring disposed about the hollow shaft.

20 Claims, 6 Drawing Sheets

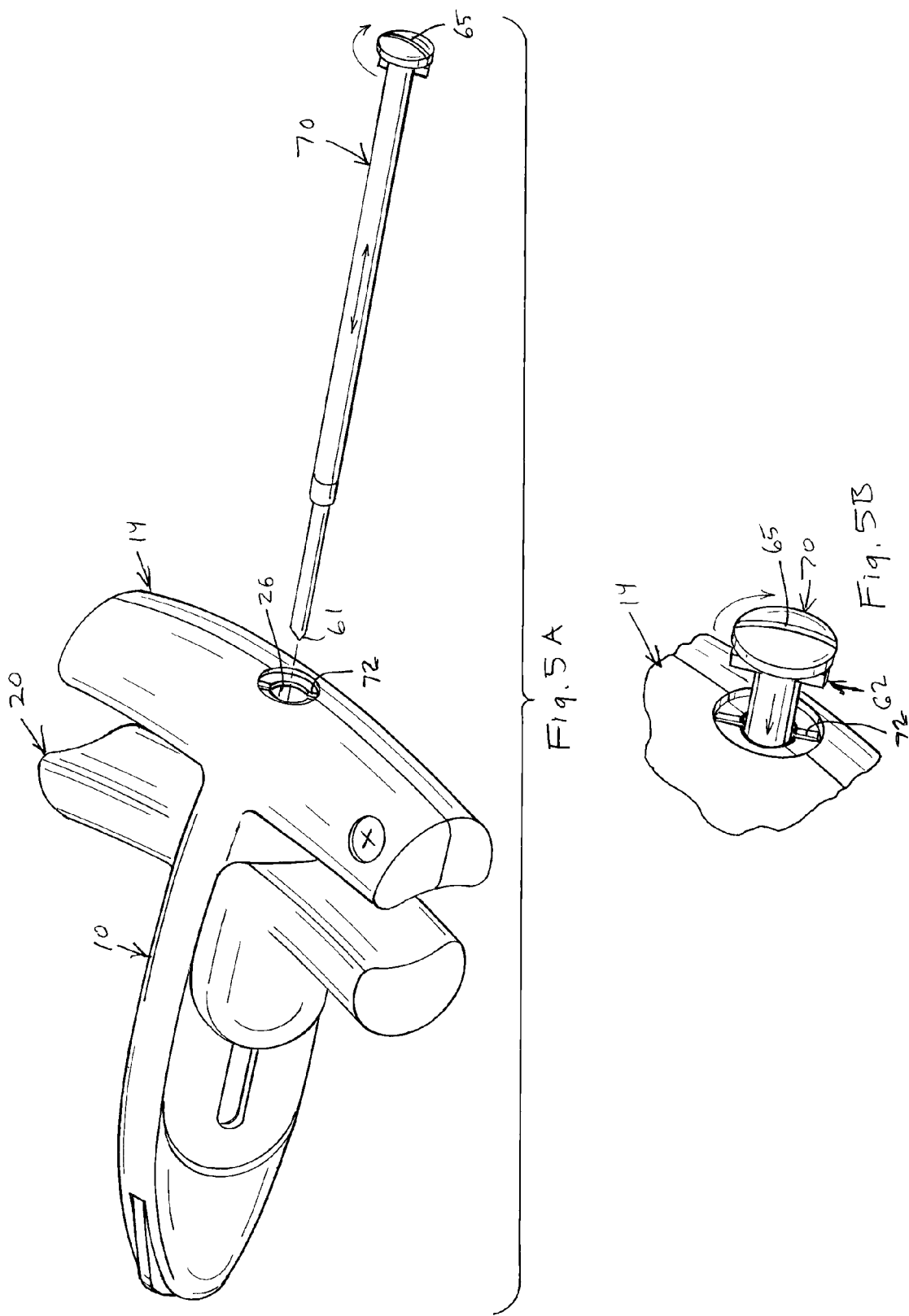

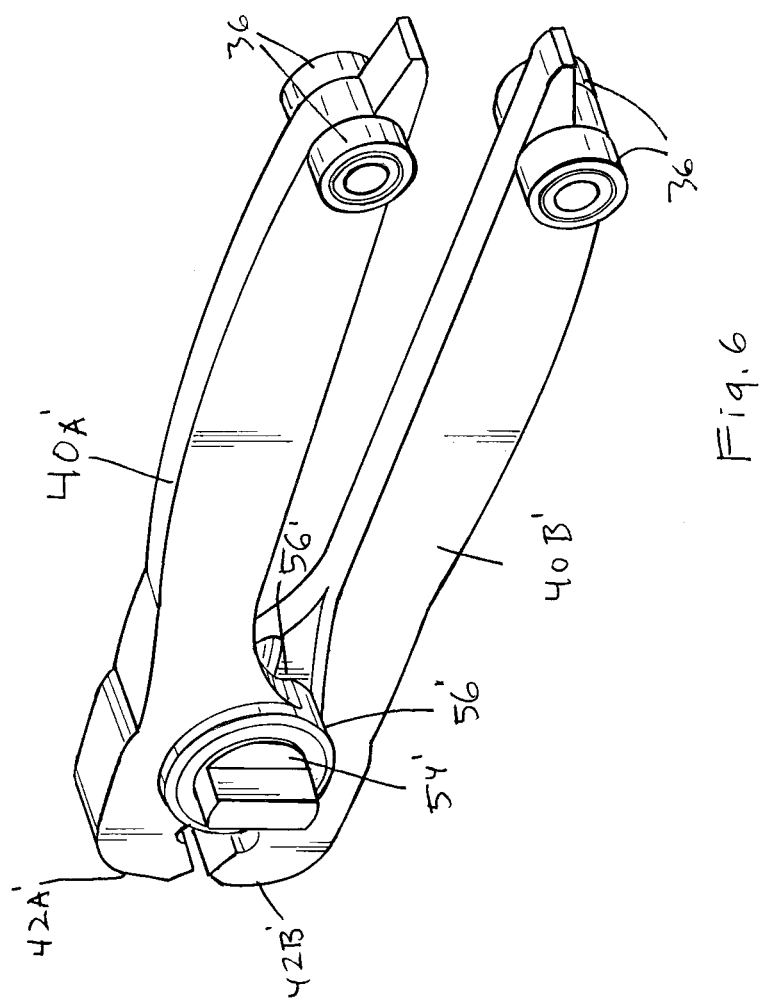

PIN CUTTER

RELATED APPLICATIONS

Priority for this application is hereby claimed under 35 U.S.C. §119(e) to commonly owned and U.S. Provisional Patent Application No. 61/389,824 which was filed on Oct. 5, 2010 and which is incorporated by reference herein in its entirety.

FIELD OF THE INVENTION

The present invention relates to a pin cutter. More particularly, the present invention relates to a pin cutter that is usable in connection with a variety of different types of surgery.

BACKGROUND OF THE INVENTION

There are a number of different types of surgery that require the use of a pin, or the like. This pin is typically located within the anatomy. For example, this is common in wrist surgery or other types of orthopedic surgery although, not limited thereto.

At the present time, in order to cut through a pin or shaft, the surgeon uses something akin to a pair of pliers. It is typical for the cut portion of the pin to be expelled and perhaps even form a small projectile. This causes an unsafe condition in operating room areas. Moreover, the cutting mechanism that is presently used is not completely effective and many times does not have a sufficient cutting force to provide a clean cut of the pin or shaft.

Accordingly, it is an object of the present invention to provide an improved pin or shaft cutter.

Another object of the present invention is to provide an improved pin or shaft cutter that is characterized by extremely effective means for providing a substantial force in cutting the pin or shaft.

Still another object of the present invention is to provide a pin or shaft cutter mechanism that enables storage of cut segments so as to eliminate unsafe conditions associated with the particular medical procedure.

Another object of the present invention is to provide an improved pin or shaft cutter that is characterized by having a removable inner canister that enables storage of cut segments. This canister may be disposable or re-usable.

A further object of the present invention is to provide an improved pin or shaft cutter that is readily sterilizable, that is relatively inexpensive to manufacture, that can be assembled quickly, and that is moreover characterized by an effective actuation mechanism that is easily operable by the user.

BRIEF SUMMARY OF THE INVENTION

Briefly, there is provided a pin cutter that is comprised of a housing including at a proximal end thereof a grip; an actuator handle supported at the housing; a pair of elongated blades that define at a distal end thereof a set of cutting jaws; and a ramp mechanism secured with the actuator handle for operating proximal ends of the blade members. The pin cutter preferably also includes a cartridge for collecting cut pin segments therein. This cartridge is slid within a support shaft of the pin cutter.

In accordance with other aspects of the present invention there is provided a hollow shaft extending through said housing, said ramp mechanism supported about said hollow shaft; a biasing spring disposed about said hollow shaft; a pin segment cartridge disposed within said hollow shaft; the cartridge has a locked position and an unlocked position; a roller at the proximal end of each blade for riding on opposite sides of the ramp mechanism; linkage mechanism interconnecting the respective blades and disposed closely adjacent to the jaw ends of the blade. the linkage mechanism includes a pair of links having a common support pin fixed to the housing; a cartridge for receiving cut pin segments, said cartridge disposed in said hollow shaft and releasable from an opposite end of the housing to the blades.

In accordance with the present invention there is also provided a pin cutter that includes a housing including at a proximal end thereof a grip; an actuator handle supported at the housing; a pair of elongated blades that define at a distal end thereof a set of cutting jaws; a hollow shaft extending through said housing; and a cartridge supported within said hollow shaft for receiving cut pin segments.

In accordance with other aspects of the present invention there is provided a ramp mechanism secured with the actuator handle for operating proximal ends of the blade member; a biasing spring disposed about said hollow shaft; the cartridge has a locked position and an unlocked position; a roller at the proximal end of each blade for riding on opposite sides of the ramp mechanism; a linkage mechanism interconnecting the respective blades and disposed closely adjacent to the jaw ends of the blades; the linkage mechanism includes a pair of links having a common support pin fixed to the housing; a pair of leaf springs each mounted fixed to the housing at opposed positions; each leaf spring has a free end contacting a respective blade; and each ramp mechanism has a slot for receiving respective blades.

DESCRIPTION OF THE DRAWINGS

It should be understood that the drawings are provided for the purpose of illustration only and are not intended to define the limits of the disclosure. The foregoing and other objects and advantages of the embodiments described herein will become apparent with reference to the following detailed description when taken in conjunction with the accompanying drawings in which:

FIGS. 5A and 5B are illustrations of a preferred use of a removable canister; and FIG. 6 is a perspective view of an alternate embodiment of blade members.

DETAILED DESCRIPTION

Figure 1A:
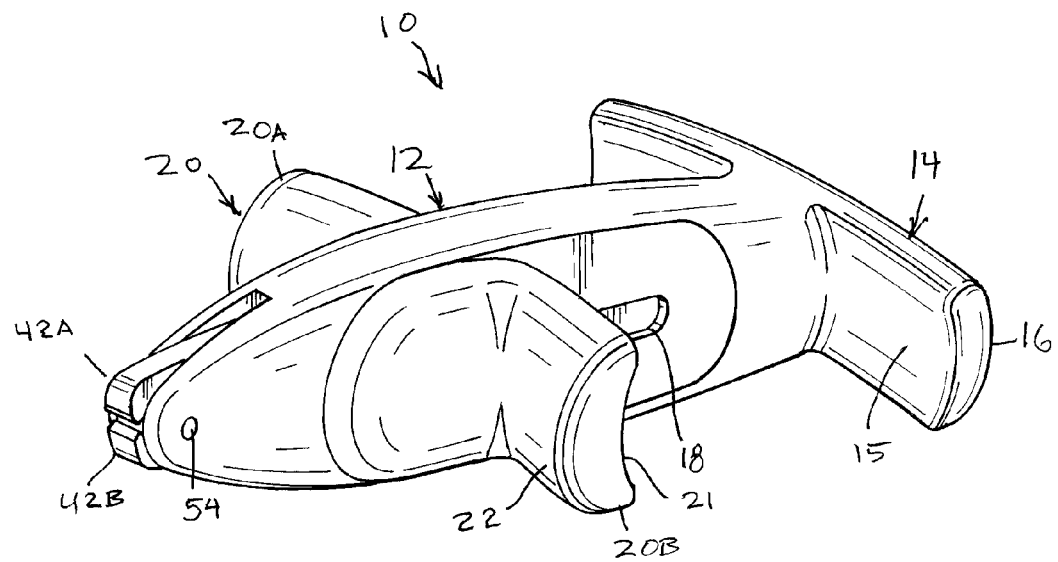
FIGS. 1A and 1B are external perspective views of the pin cutter of the present invention and respective released and actuated positions.

Reference is now made to the drawings for a preferred embodiment of the pin cutter of the present invention. This is comprised of a main body 10 that is comprised basically of a longitudinally extending housing 12 and a transverse grip 14. The combination of the housing 12 and grip 14 may be provided in two separate sections that are interconnected such as by using screws or the like which are not disclosed herein. The grip 14 is bent to fit comfortably within the palm of the user. The grip 14 thus includes a relatively flat distal side 15 and a rounded proximal side 16.

Figure 1B:
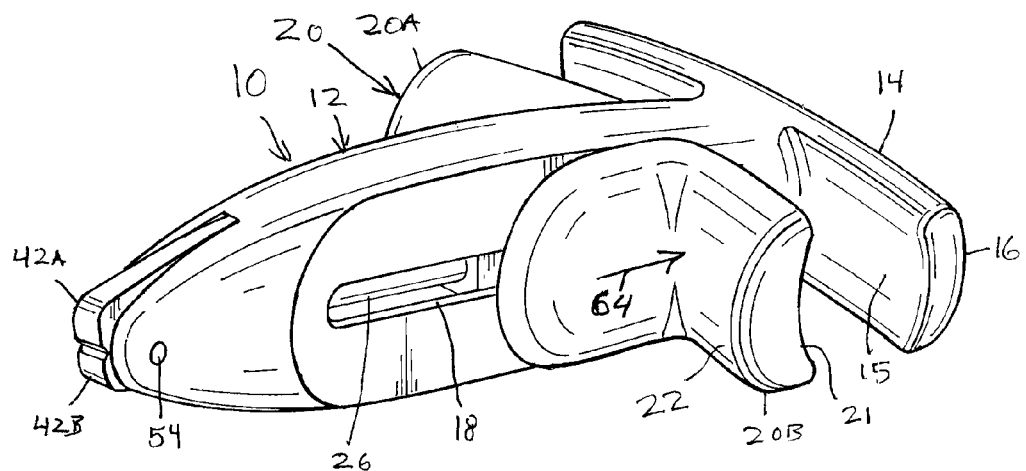
Figure 2A:
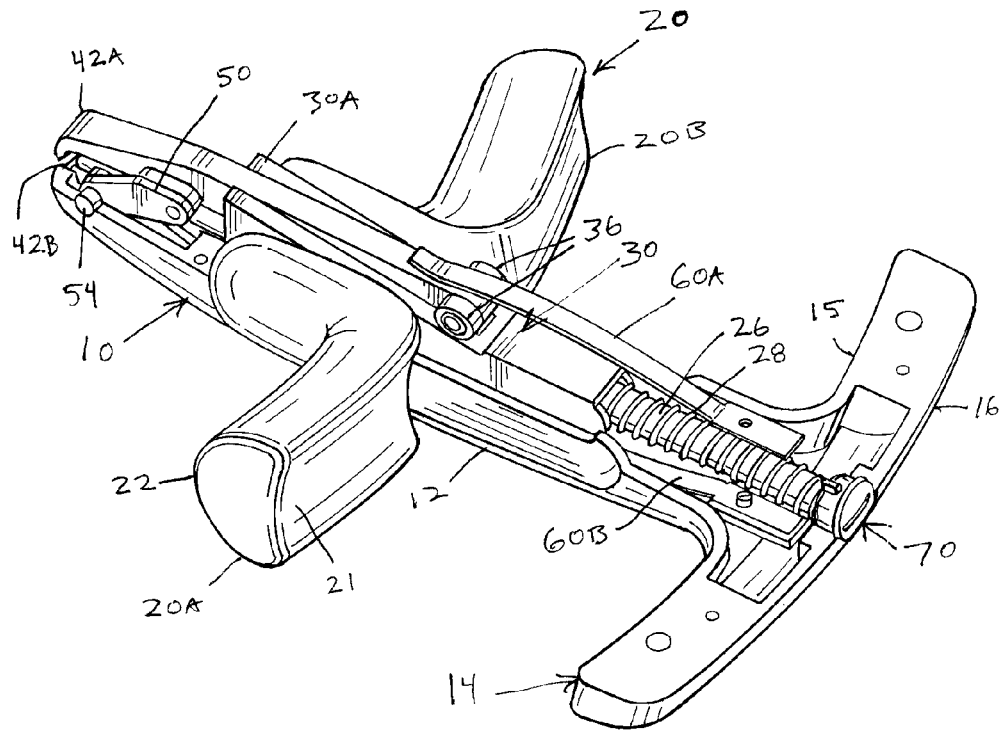
FIGS. 2A and 2B are perspective cut-away views of the device and respective released and actuated positions.
Figure 2B:
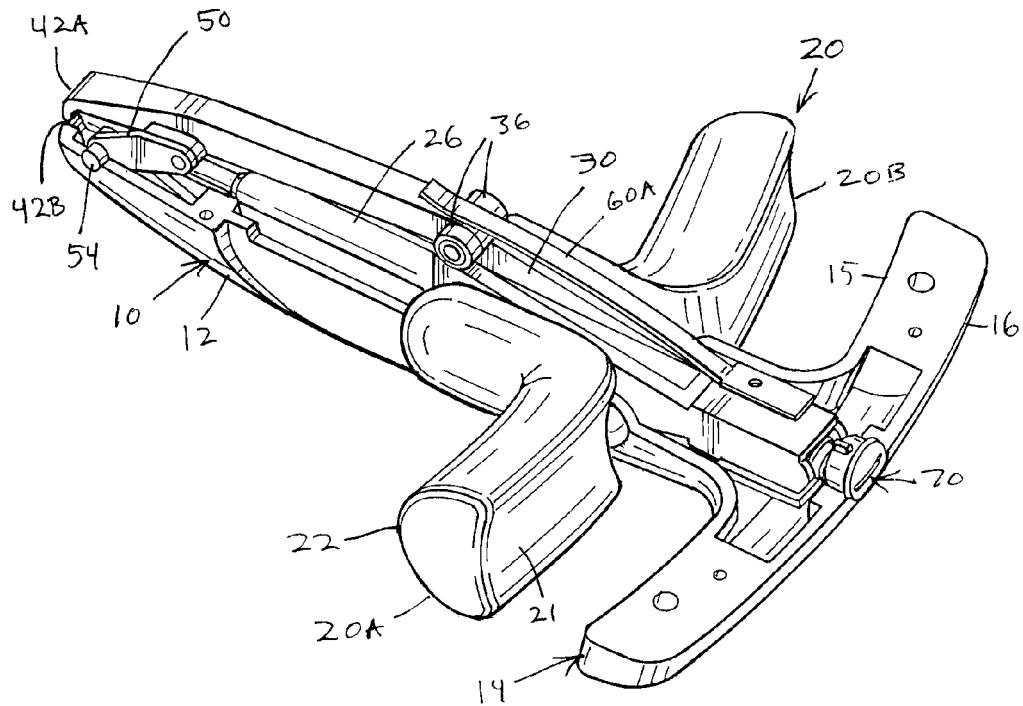
Figure 3A:
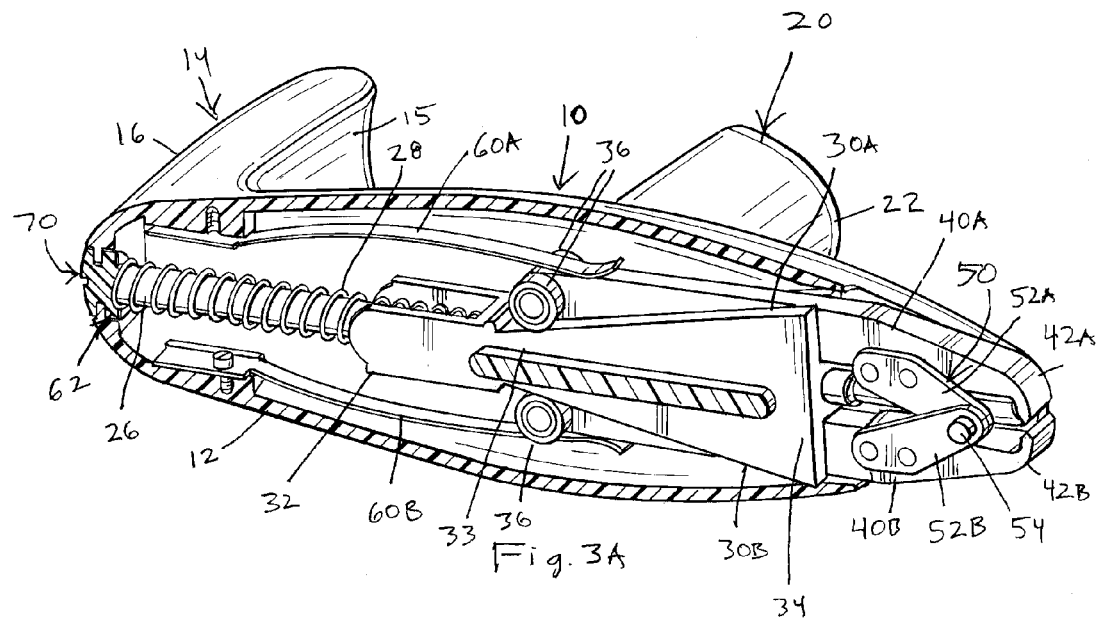
FIGS. 3A and 3B are further longitudinal perspective cut-away views of the device in the respective released and actuated positions.
Figure 3B:
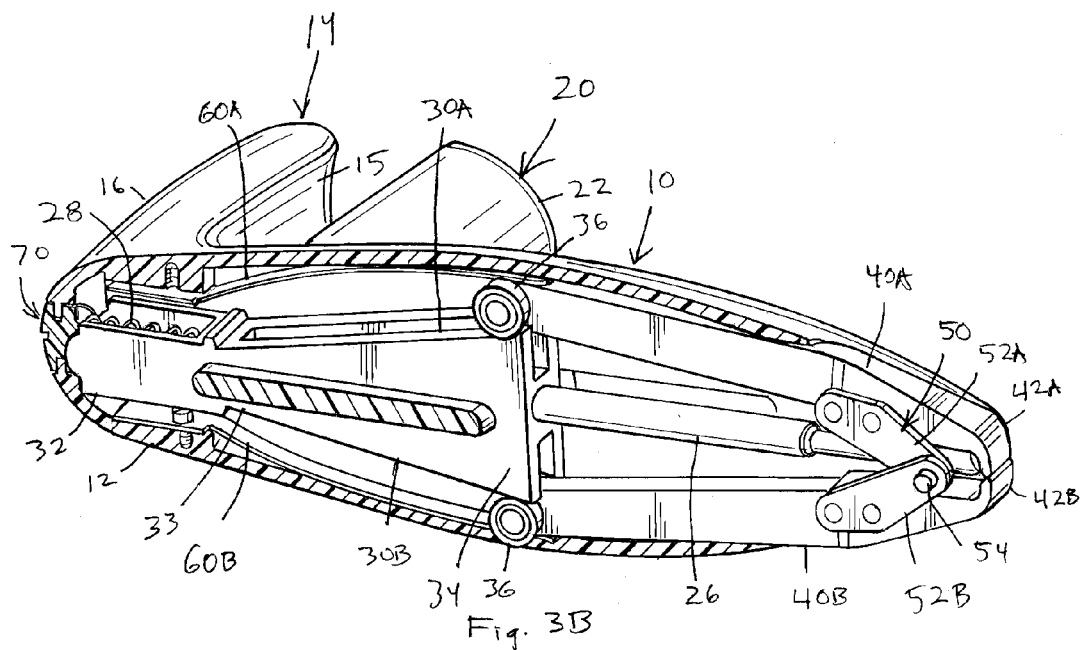
Figure 4A:
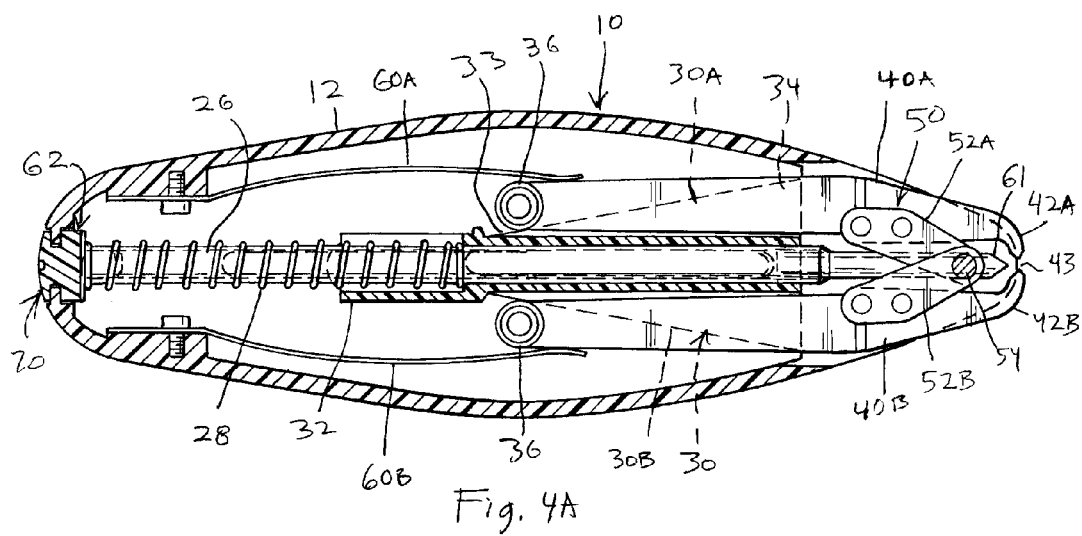
FIGS. 4A and 4B are side elevation views of the device and respective released and actuated positions.
Figure 4B:
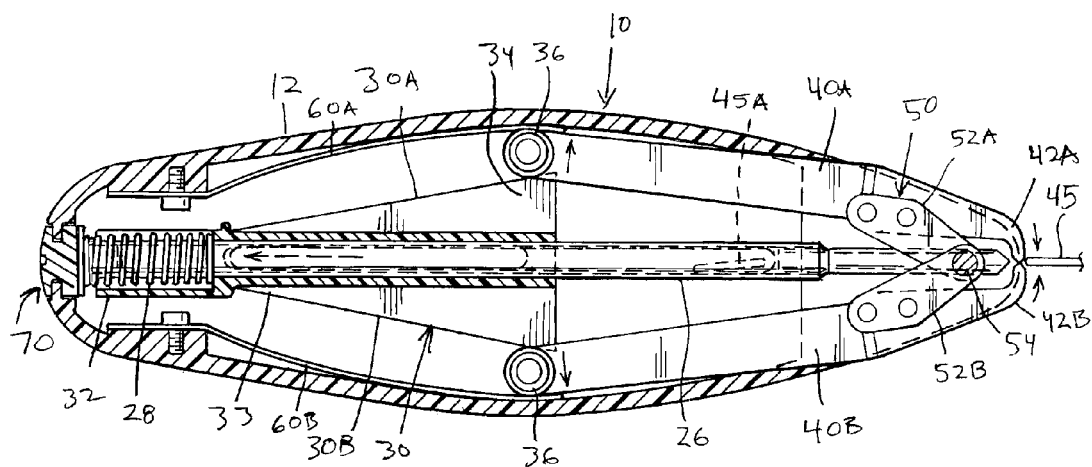

The longitudinally extending housing 12 is basically hollow but is also provided with opposed slots 18 as illustrated in FIGS. 1A and 1B. The slots 18 accommodate the actuation lever 20. The actuation lever 20 is actually provided in separate interconnected actuator sections 20A and 20B. The actuation lever 20 is also provided with a substantially flat surface 21 and a more rounded surface 22. The operator's fingers would engage the rounded surface 22. As the separate segments of the actuation lever are interconnected, the actuation lever moves the separate sections in unison as the actuation lever is moved from the position shown in FIG. 1A, for example, to the position shown in FIG. 1B. The actuation lever 20 may also be referred to as a handle. Other views, such as FIGS. 2A and 2B also illustrate the respective positions of the handle 20. FIG. 2A shows the handle 20 and its release position, while FIG. 2B shows the handle 20 drawn rearwardly toward the grip 14 to actuate and close the pin cutter's blades. FIGS. 3A and 3B also show similar respective rest and actuated positions. In FIG. 3A it is noted that the blades 42 are partially open while in FIG. 3B the very ends of the blades are closed. Similar positions are also illustrated in FIGS. 4A and 4B. Also see in FIGS. 3A and 3B wherein each ramp mechanism has a slot for receiving respective blades. The slots are disposed on opposed sides of the ramp mechanism. FIG. 3A in particular depicts the respective blades disposed in these slots.

Within the housing 12, there is supported an elongated shaft 26. This shaft 26 extends between front and rear ends of the housing 12 and is preferably hollow so that it can also function, or receive a cartridge for the portions 45A of pin 45 that are cut at the distal blade. As illustrated, in, for example, FIG. 2A, a biasing spring 28 is disposed about the shaft 26. The spring 28 biases the actuation handle 20 to its rest position such as illustrated in FIG. 2A. At one end the coil spring 28 is secured at the grip 14. At the other end, the coil spring 28 engages the movable ramp 30. The ramp 30 essentially connects with the handle 20 so that any movement of the handle 20 in a proximal distance likewise moves the ramp 30 in the same direction.

Reference may be made to, for example, FIG. 3A that shows the general construction of the ramp 30. The ramp 30 is, as mentioned previously, integral with the actuation handle and may be supported for longitudinal motion on the hollow shaft 26. The ramp 30 includes a proximal end 32 that is for support of one end of the bias spring 28. The other end of the ramp 30 is constructed with a ramp configuration progressing from a smaller width at 33 to a wider width at 34. The proximal ends of the blades are adapted to ride on opposed surfaces 30A and 30B of the ramp 30. In this regard, in FIG. 4A the proximal ends of the blades at the roller 36 are disposed, in the rest position of the handle, at the bottom of the ramp surfaces 30A, 30B. On the other hand, when the handle is depressed, then the ramp 30 is moved to the position illustrated in FIG. 4B with the proximal ends of the blades at the bearing 36 at the uppermost portion of the ramp surfaces 30A, 30B.

The drawings also illustrate, such as in FIGS. 4A and 4B, the elongated blade members 40 which are illustrated in the drawings as respective blade members 40A and 40B. At the very proximal end of each of these elongated blades, there is supported the roller bearing 36. As indicated previously, operation of the actuation handle in turn moves the ramp 30 such as from the position of FIG. 4A to the position of FIG. 4B. This causes the respective roller bearings 36 on surfaces 30A, 30B to progress to a point where they are at the widest portion 34 of the ramp. This, in turn, causes the blade members 40A, 40B to spread at their proximal ends.

The blade members 40A and 40B also form at their distal ends the cutting portions 42A and 42B (jaws). In the position illustrated in FIG. 4A, wherein the roller bearings are at the minimal width of the ramp, then the blades 42A, 42B are spaced apart as indicated by the gap 43 in FIG. 4A. On the other hand, when the blade members 40A and 40B are pivoted to the position illustrated in FIG. 4B, then the end blade members 42A, 42B close causing an associated pin 45 to be severed. The hollow shaft 26 which can form a cartridge, or a separate cartridge 70, can be inserted within the shaft 26 for capturing the cut segment 45A of the pin 45.

In this way, any small sections 45A of the pin that are cut or severed are captured by the cutting mechanism. Refer to FIGS. 5A and 5B hereinafter for further details of the cartridge or canister that is used for the collection of pin segments 45A.

The operation of the blade members 40A, 40B is controlled from a linkage 50. There are actually a pair of linkages 50, one on each side of the blade members. Each of the linkages 50 includes a pair of links 52 such as the links 52A and 52B illustrated in FIG. 3A. At one end, each of the links 52 is secured to an associated blade member. The links 52A and 52B are joined at a hinge pin 54. See also the hinge pin 54 that, not only supports the links 52A and 52B, but is also fixed in position at the housing 12 (see FIGS. 2A and 2B). This link mechanism 50 operates so that as the proximal ends of the blade members spread, the jaws 42A, 42B of the blade members close such as illustrated in the position of FIG. 4B.

The pin cutter mechanism of the present invention also preferably employs a pair of leaf springs 60A, 60B. These leaf springs impose a force upon the respective blade members 40A, 40B so that the blade members will be biased towards a closed position but still be controlled by virtue of the actuation handle 20 and the associated ramp member 30. Each of the leaf springs 60A, 60B is supported at a proximal end thereof in a fixed position within the housing 12. The very distal end of each of the leaf springs 60A, 60B is urged against a surface of the respective blade members 40A, 40B. Reference to FIGS. 4A and 4B illustrate the position of the leaf springs 60A, 60B. In both positions of FIGS. 4A and 4B, it is noted that the distal end of the leaf springs still urges against the associated blade member.

Thus, in operation, and with reference to FIGS. 1A and 1B, normally the handle 20 is positioned in the location of FIG. 1A. This means that the handle 20 is in its more distal position. In order to operate the cutting blades so that they are closed and cut the pin, the handle 20 is moved in the direction of arrow 64 to the position of FIG. 1B. The mechanism of the present invention is readily usable by a single hand of the user. The grip 14 is generally placed in the palm and fingers are then placed on the opposite sections of the actuator handle 20. The actuator handle 20 is thus moved in the direction of arrow 64 toward the grip 14. This causes a closure of the jaws 42A, 42B. The combination of the ramp, and the closure of the blade members creates a substantial force at the jaws 42A, 42B. This is further evidenced by the hinge pin 54 support of the linkage 50. The hinge pin 54 is preferably close to the jaws so as to provide a substantial force momentum arm. Thus, by a sliding action of the actuator handle 20, a substantial force is imposed at the jaws 42A, 42B. This force is at least 80 pounds imposed at the jaws but based on a smaller force necessary at the actuation handle.

Reference is now made to FIGS. 5A and 5B for further details of the use of a preferred disposable or re-useable canister or cartridge that is used to collect cut pin segments 45A. This cartridge 70 is shown in FIG. 5A withdrawn from the pin cutter. It is hollow and can accommodate several pin segments 45A therein (see FIG. 4B). The cartridge 70 is meant to slide within the shaft 26 with the very distal end 61 thereof disposed immediately adjacent to the jaws 42A, 42B. The end 61 is illustrated in FIG. 4A. The end 61 is open to receive the pin segments as they are cut by the jaws. The very proximal end of the cartridge 70 is provided with a locking means at 62 in the form of a ridge that can interlock with a slot 72 in the grip 14. The cartridge 70 is locked in place by rotating it a partial turn in the slot, and can be likewise released by rotation in the opposite direction. Engagement means, such as a slot 65 is provided so that the cartridge can be rotated between locked and unlocked positions. In place of the bayonet type lock shown in the drawings, other locking arrangements can be used. For example, a force or interference fit may be used; a snap fit mechanism may be used; a screw mechanism may be used; or any other known holding arrangements for keeping the cartridge in place, while still allowing an easy release of the cartridge.

Reference is now also made to FIG. 6 which shows an alternate embodiment of the blade members 40A', 40B' with respective jaws 42A', 42B' that are formed with respective bosses 56' replacing linkages 50 as a connection to hinge pin 54'. In this alternate pivot mechanism opposed ends of the pin 54' are secured in opposed sides of the housing. The bosses 56', one associated with each blade member, are integrally formed with its corresponding blade member. The blade members are able to readily pivot on the pin 54'. The pin 54' is also preferably provided with a center passage (not shown) for receiving the cartridge.

Having now described one preferred embodiment of the present invention, it should be apparent to those skilled in the art that numerous other embodiments and modifications thereof are contemplated as falling within the scope of the present invention as defined by the appended claims.

What is claimed is:

1. A pin cutter comprising:
a housing including a grip at a proximal end;
an actuator handle supported at the housing;
a pair of elongated blades defining a set of cutting jaws and provided at a distal end of the housing;
a ramp mechanism secured with the actuator handle for operating proximal ends of the blade member;
a hollow shaft extending through said housing, said ramp mechanism supported about said hollow shaft;
a roller at the proximal end of each blade for riding on opposite sides of the ramp mechanism;
a linkage mechanism interconnecting the respective blades and disposed closely adjacent to the jaw ends of the blades;
wherein said linkage mechanism includes a pair of links having a common support pin fixed to the housing; and
a cartridge for receiving cut pin segments, said cartridge disposed in said hollow shaft and releasable from an opposite end of the housing to the blades.

2. The pin cutter of claim 1 wherein the cartridge has a locked position and an unlocked position.

3. A pin cutter comprising:
a housing including a grip at a proximal end;
an actuator handle supported at the housing;
a pair of elongated blades defining a set of cutting jaws and provided at a distal end of the housing;
a ramp mechanism secured with the actuator handle for operating proximal ends of the blade member;
a hollow shaft extending through said housing;
a roller at the proximal end of each blade for riding on opposite sides of the ramp mechanism; and
a cartridge for receiving cut pin segments, said cartridge disposed in said hollow shaft and
releasable from an opposite end of the housing to the blades.

4. The pin cutter of claim 3 wherein said ramp mechanism is supported about said hollow shaft and is supported for longitudinal motion on the hollow shaft.

5. The pin cutter of claim 4 including a biasing spring disposed about said hollow shaft.

6. The pin cutter of claim 5 wherein said ramp mechanism includes separate ramps having respective slots therebetween for receiving respective elongated blades.

7. The pin cutter of claim 3 wherein the cartridge has a distal open end that is disposed adjacent to the cutting jaws.

8. The pin cutter of claim 7 wherein the cartridge also includes an end lock for engagement with a slot in the grip.

9. The pin cutter of claim 3 further comprising a linkage mechanism that includes a pair of links having a common support pin fixed to the housing.

10. The pin cutter of claim 3 wherein said housing comprises a longitudinally extending housing and the grip comprises a transverse grip including a piar of grip arms.

11. The pin cutter of claim 3, wherein the actuator handle comprises an actuator structure.

12. The pin cutter of claim 11, wherein the actuator structure includes separate actuator sections on respective sides of the housing and the housing has respective side slots for accommodating the separate actuator sections.

13. A pin cutter comprising:
a housing including a grip at a proximal end;
an actuator handle supported at the housing;
a pair of elongated blades defining a set of cutting jaws and provided at a distal end of the housing;
a hollow shaft extending through said housing;
a cartridge supported within said hollow shaft for receiving cut pin segments;
a ramp mechanism secured with the actuator handle for operating proximal ends of the blade member;
a biasing spring disposed about said hollow shaft; wherein the cartridge has a locked position and an unlocked position; and
a roller at the proximal end of each blade for riding on opposite sides of the ramp mechanism.

14. The pin cutter of claim 13 including a linkage mechanism interconnecting the respective blades and disposed closely adjacent to the jaw ends of the blades.

15. The pin cutter of claim 14 wherein said linkage mechanism includes a pair of links having a common support pin fixed to the housing.

16. The pin cutter of claim 15 including a pair of leaf springs each mounted fixed to the housing at opposed positions.

17. The pin cutter of claim 16 wherein each leaf spring has a free end contacting a respective blade.

18. The pin cutter of claim 17 wherein each ramp mechanism has a slot for receiving respective blades.

19. The pin cutter of claim 13 including a hinge pin for connecting proximal ends of the respective blades.

20. The pin cutter of claim 19 wherein each blade has a corresponding end boss connected at said hinge pin.

\* \* \* \* \*